(12) United States Patent
Franklin et al.

(10) Patent No.: US 10,357,615 B2
(45) Date of Patent: Jul. 23, 2019

(54) SYRINGE EXTRUSION ACCESSORY

(71) Applicant: Allergan, Inc., Irvine, CA (US)

(72) Inventors: Ethan W. Franklin, Santa Barbara, CA (US); Justin J. Schwab, San Francisco, CA (US)

(73) Assignee: ALLERGAN, INC., Irvine, CA (US)

( * ) Notice: Subject to any disclaimer, the term of this patent is extended or adjusted under 35 U.S.C. 154(b) by 307 days.

(21) Appl. No.: 15/011,897

(22) Filed: Feb. 1, 2016

(65) Prior Publication Data
US 2016/0144125 A1 May 26, 2016

Related U.S. Application Data

(63) Continuation of application No. 14/284,285, filed on May 21, 2014, now abandoned.
(60) Provisional application No. 61/826,878, filed on May 23, 2013.

(51) Int. Cl.
*A61M 5/315* (2006.01)
*A61M 5/31* (2006.01)
*A61M 5/50* (2006.01)

(52) U.S. Cl.
CPC ...... *A61M 5/31556* (2013.01); *A61M 5/3137* (2013.01); *A61M 5/31555* (2013.01); *A61M 5/31581* (2013.01); *A61M 5/5013* (2013.01); *A61M 2005/3139* (2013.01)

(58) Field of Classification Search
CPC .......... A61M 5/31556; A61M 5/31568; A61M 5/31576; A61M 5/3158; A61M 5/3137; A61M 5/31581; A61M 5/31526; A61M 2005/3139
See application file for complete search history.

(56) References Cited

U.S. PATENT DOCUMENTS

| | | | |
|---|---|---|---|
| 3,517,668 A * | 6/1970 | Brickson | A61D 7/00 222/309 |
| 4,444,560 A * | 4/1984 | Jacklich | A61M 5/31595 222/391 |
| 4,710,172 A | 12/1987 | Jacklich et al. | |
| 4,779,770 A * | 10/1988 | Herold | A61M 5/31581 222/391 |
| 5,433,352 A * | 7/1995 | Ronvig | A61M 5/31581 222/391 |
| 2003/0078912 A1* | 4/2003 | Oliver | A61M 31/00 |
| 2005/0192544 A1* | 9/2005 | Wolbring | A61M 5/31501 604/218 |

(Continued)

FOREIGN PATENT DOCUMENTS

| | | |
|---|---|---|
| FR | 2857654 A1 | 1/2005 |
| WO | 1994012228 A1 | 6/1994 |

(Continued)

*Primary Examiner* — Bhisma Mehta
*Assistant Examiner* — James D Ponton
(74) *Attorney, Agent, or Firm* — Nathan S. Smith; Morgan, Lewis & Bockius LLP

(57) ABSTRACT

Described herein are syringe extrusion accessories comprising: a handle operatively coupled to an attachment portion configured to attach to a syringe; and at least one pawl operatively coupled to the handle and configured to engage with a plunger of the syringe, wherein the syringe extrusion accessory is configured to transfer a substantially perpendicular force applied to the handle to an axial force to push the plunger and extrude a product from the syringe.

8 Claims, 2 Drawing Sheets

(56) References Cited

U.S. PATENT DOCUMENTS

| | | | | |
|---|---|---|---|---|
| 2005/0215956 A1* | 9/2005 | Nerney | ............... | A61M 5/3148 604/218 |
| 2013/0018325 A1* | 1/2013 | Schiller | ............... | A61M 5/3137 604/198 |
| 2014/0012227 A1* | 1/2014 | Sigg | ...................... | A61M 5/178 604/506 |

FOREIGN PATENT DOCUMENTS

| | | |
|---|---|---|
| WO | 2002055135 A2 | 7/2002 |
| WO | 2013005881 A1 | 1/2013 |

* cited by examiner

SYRINGE EXTRUSION ACCESSORY

CROSS REFERENCE TO RELATED APPLICATIONS

This application is a continuation of U.S. patent application Ser. No. 14/284,285, filed May 21, 2014 which claims the benefit of U.S. provisional patent application Ser. No. 61/826,878, filed May 23, 2013, the entire disclosure of each of which is incorporated herein by this specific reference.

FIELD

The present invention generally relates to medical injection device accessories, and more specifically relates to a medical syringe accessory designed to facilitate aliquot dosing.

BACKGROUND

The ability to accurately assess correct injection dosage is most commonly associated with visual cues. For example, volumetric marks already come printed or etched on the side of conventional syringe bodies, and this remains the most common form of measurement. A practitioner injects a certain amount of a substance, such as a drug, by verifying fluid level using these volumetric marks.

Even more generally, a physician can intake an amount of a drug to be injected into the syringe using the volumetric marks. Then, a practitioner can simply expel the entire volume into a patient in a single plunger run. Such a full expulsion of drug removed the need to only inject a portion of a drug in a syringe. Thus, for pharmaceutical drugs, the benefits of injecting the correct dosage should not require explanation.

However, in applications using sensitive drugs such as botulinum toxin or aesthetic soft tissue fillers, for example, hyaluronic acid-based dermal fillers such as Juvederm® XC, manufactured by Allergan, Inc., dose indication provides the practitioner with additional control over precise facial sculpting.

Additionally, with applications like botulinum toxin, injection of multiple small, precise doses of toxin may be advantageous over injection of a large bolus of the material.

Further, with fat grafting, injection of multiple small, precise doses of fat cell-containing material may be advantageous over injection of a single large bolus of the material. Smaller bolus injection increases retention of the injected material, possibly by providing greater vascularization of the material throughout the fat cells and improving survivability thereof. Injection of a large bolus is less likely to be retained long term as the injected fat cells may be more prone to die, due to lack of vascularization, for example.

Many of these injectable materials, for example, dermal fillers and fat grafting materials, are not easily extruded through standard syringes and accompanying cannula. These materials tend to provide significant resistance to be pushed through a narrow cannula. The problem is even more exacerbated by the fact that these materials are often used for detailed precision work in facial contouring and body sculpting.

Injection devices, both manual and motorized, have been specifically developed, or at least proposed, to address these issues. Interestingly, many physicians prefer the use of manual conventional syringe injectors over electronically controlled, motorized devices. For at least this reason, there remains a need for devices (e.g., simple devices) that can be attached to a standard syringe and which provide better control over small aliquot dosing of relatively difficult to inject materials, for example, dermal fillers, fat grafting materials and the like.

SUMMARY

Disclosed herein are mechanical dosing accessories and/or syringe extrusion accessories configured to be attached to, coupled to, or incorporated into standard syringes. The dosing accessories are configured to provide improved mechanical advantage or leverage and dosing capability, relative to a conventional syringe alone. In some embodiments, the accessories described can be used in conjunction with conventional syringes for injection of substances. The substances or products can be highly viscous such as, but not limited to, dermal fillers or fat grafting materials.

In one embodiment described herein are syringe extrusion accessories. The accessories can include: a handle operatively coupled to an attachment portion configured to attach to a syringe; and at least one pawl operatively coupled to the handle and configured to engage with a plunger of the syringe. The syringe extrusion accessory can be configured to transfer a substantially perpendicular force applied to the handle to an axial force to push the plunger and extrude a product from the syringe.

Other embodiments include methods of using the syringe extrusion accessories. The methods describe extruding a product from a syringe. The methods include: applying a substantially perpendicular force to an accessory associated with the syringe thereby extruding the product from the syringe. The accessories can include a handle operatively coupled to an attachment portion configured to attach to a syringe; and at least one pawl operatively coupled to the handle and configured to engage with a plunger of the syringe. The handle can include one or more depressions configured to apply force from at least one finger.

In some embodiments, the methods can be used with the accessory which is configured to transfer a substantially perpendicular force applied to the handle to an axial force to push the plunger and extrude the product from the syringe. The accessory can be attached to the syringe's flange by a snap fit, a friction fit, a glue, an adhesive, or a combination thereof.

The at least one pawl described herein can include at least one claw which can be configured to engage with the syringe's plunger. The pawl can also have a sinusoidal shape.

The accessory includes a handle which can be coupled to the attachment portion through a hinge. In other embodiments, the pawl is also coupled to the handle through a hinge. The pawl can further be attached to the handle with a spring, such as a compression spring.

The accessories described herein can attach to any portion of a syringe. In some embodiments, the accessories can attach or be configured to attach to a flange associated with the syringe.

BRIEF DESCRIPTION OF THE DRAWINGS

Embodiments of the present description are illustrated by way of example, and not by way of limitation, in the figures of the accompanying drawings and in which like reference numerals refer to similar elements, wherein.

DETAILED DESCRIPTION

Generally described are syringe accessories such as, but not limited to mechanical dosing accessories and/or syringe extrusion accessories that can be attached to a conventional syringe and provide a transfer of perpendicular force to axial force for injection. In other embodiments, an accessory as described herein can be permanently mounted to a syringe using, for example, glue or adhesive. In still other embodiments, a syringe including an accessory as described herein can be produced as a single integrated device.

Figure 1:
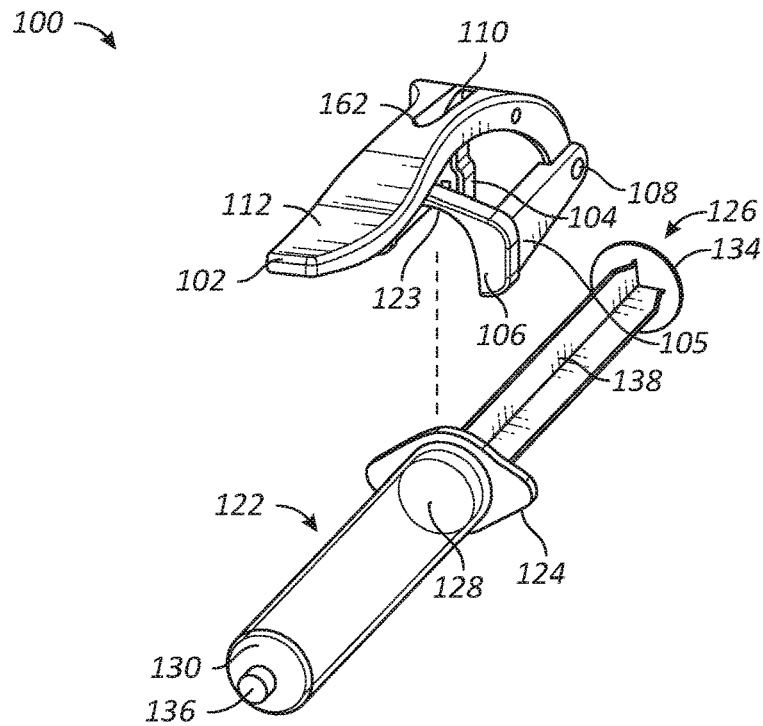
FIG. 1 illustrates a perspective view of a syringe and a syringe extrusion accessory as described herein.
Figure 2:
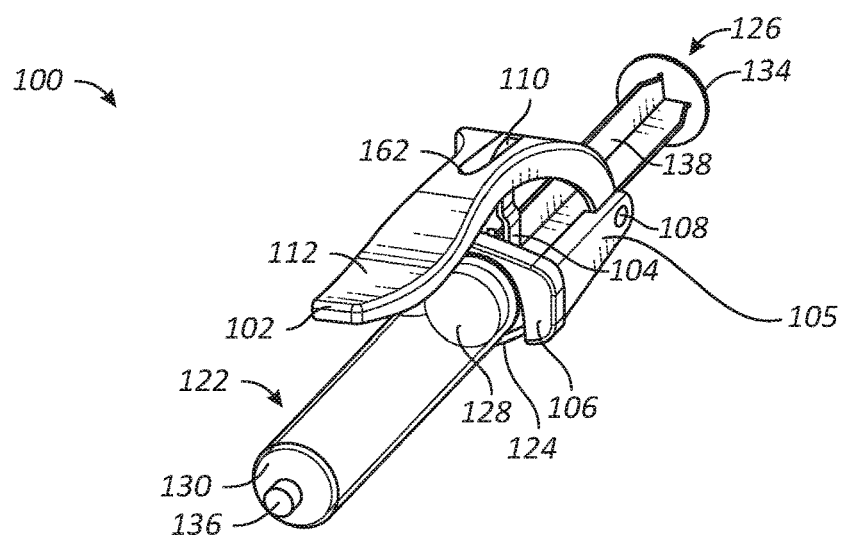
FIG. 2 illustrates a perspective view of a syringe with an extrusion accessory as illustrated in FIG. 1 attached thereto.

As illustrated in FIGS. 1-2, an accessory 100 as described herein can generally include handle 102, pawl 104, arm member 105, attachment portion 106, a first hinge 108 and a second hinge 110.

Handle 102 can optionally include a finger indentation region 112 wherein a user can apply a substantially perpendicular force to a depressed portion thereby focusing the force to a substantially predetermined point on handle 102. Handle 102 can be configured to accept a substantially perpendicular input force and transfer that force to pawl 104.

Pawl 104 is operably attached to handle 102 through second hinge 110. Pawl 104 can have a generally sinusoidal shape having a first end 114 terminating at second hinge 110 and second end 116 terminating at one or more claws 118. First end 114 can be curved toward the proximal end 130 of syringe 122 when fully extended in use thereby achieving the translation of force provided by the accessories. Second end 116 can be curved toward the distal end of syringe 122 when fully extended in use.

Pawl 104 can be operably configured to move one or more claws 118 in generally axial direction 120. Pawl 104 can include one, two, three, four, five, six, seven, eight, nine, ten, eleven, twelve, 13, 14, 15, 16, 17, 18, 19, 20, or more claws. As such, based on substantially perpendicular movement of handle 102, claws 118 can in turn be moved in axial direction 120 through second hinge 110.

Further, handle 102 is operably connected to attachment portion 106 via one or more arm members 105 through first hinge 108. Attachment portion 106 is configured to allow attachment of accessory 100 to syringe 122. In one embodiment, accessory 100 can be attached to syringe 122 at flange 124 within a cavity 123 of the attachment portion 106. Attachment portion 106 can be shaped to at least partially engage flange 124. In some embodiments, attachment portion 106 can engage between about 20% and about 80%, between about 30% and about 60%, between about 40% and about 60%, between about 50% and about 70%, or between about 60% and about 80% of flange 124. Attachment portion 106 can engage with flange 124 using a friction fit, a locking fit where attachment portion 106 includes locking features that snap and lock once the two parts are engaged, or a glue engagement wherein attachment portion 106 and flange 124 are glued together.

Substantially perpendicular force applied to handle 102 can be translated to force in axial direction 120. Claws 118 can engage plunger 126 and provide an axial force thereby driving plunger head 128 toward proximal end 130 of syringe 122.

Substantially perpendicular force can be applied at an angle 132 which is substantially perpendicular to syringe 122. Angle 132 can be about 1 degree, about 5 degrees, about 10 degrees, about 15 degrees, about 20 degrees, about 25 degrees, less than about 5 degrees, less than about 10 degrees, less than about 15 degrees, between about 1 degree and about 10 degrees, between about 1 degree and about 20 degrees, or between about 5 degrees and about 25 degrees.

This substantially perpendicular force can replace axial forces that typically must be applied to plunger finger surface 134. With highly viscous materials such as dermal fillers and fat grafting substances, substantial axial forces must be applied in order to extrude these materials from a needle or other delivery device attached to luer tip 136 or other attachment interface. This need to apply a substantial force to plunger finger surface 134 requires a user to balance applying axial forces to the syringe with resisting axial forces of a needle into the tissue.

In some embodiments, luer tip 136 or other attachment interface can be configured to attach to a cannula or needle which is suitable for introducing contents of syringe 122 into a target region of a patient for tissue bulking, augmentation or reconstructive purposes.

In other embodiments, luer tip 136 or other attachment interface can be configured to attach to flexible tubing or a conduit which is suitable for introducing contents of syringe 122 into a target region of a patient for tissue bulking, augmentation or reconstructive purposes. Such embodiments may allow for enhanced flexibility and ergonomic grip of a cannula or a needle.

A cannula or a needle as used herein can be a 10, 12, 14, 16, 18, 20, 22 up to 33 gauge, or other gauges. In some embodiments, the needle gauge may be one suitable for fat grafting or dermal filler purposes. In one embodiment, the needle gauge is between 10 and 33. The length of a needle can be any appropriate length known in the art. In one embodiment, the needle length is about 1/16 inch to about 3 inches, more generally about 1/16 inch to about 2 inches. A cannula or a needle may be blunt or sharp tipped.

Pawl 104 can be configured to engage with a given plunger style. Plungers can have various shapes for stem portion 138. For example, as illustrated in the Figures, stem 138 includes vertical appendage 140 and horizontal appendage 142. Thus, in one embodiment, pawl 104 can be split at second end 116 thereby straddling vertical appendage 140 without touching it and engaging both sides of horizontal appendage 142.

In other embodiments, stem portion 138 may have a cylindrical shape or circular cross-section. In such embodiments, pawl 104 can have a single second end 116 or an un-split second end. This single second end 116 can engage stem portion 138 along its cylindrical surface.

Various other stem shapes can be used and skilled artisans will understand how to modify pawl 104 to engage these types of plungers and translate substantially perpendicular force to axial force on the plunger.

In some embodiments, spring 144 can be provided to couple pawl 104 to handle 102 as illustrated in FIGS. 3-6.

Figure 6:
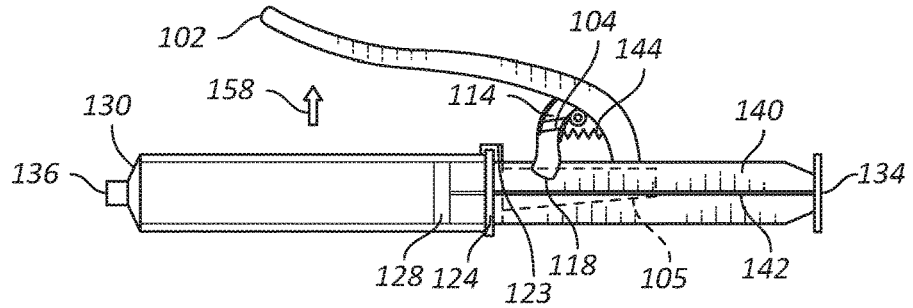
FIG. 6 illustrates a reset of the extrusion accessory to extrude a further amount of substance from the syringe.

Spring 144 can provide a resistive or compressive force as handle 102 is depressed. When handle 102 is disengaged, thereby disengaging pawl 104 from plunger 126, spring 144 can compress thereby pulling pawl 104 toward handle 102 as illustrated in FIG. 6 thereby "re-setting" the device.

Figure 5:
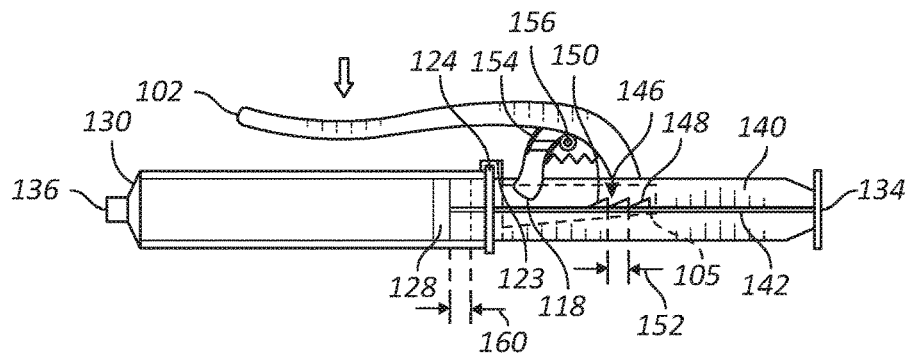
FIG. 5 illustrates a third step in using an extrusion accessory wherein a substantially perpendicular force is applied to the accessory's handle until the pawl can no longer extend from the handle indicating the end of an injection sequence.

In some embodiments, tracks can be provided on plunger 126 for claws 118 to engage. For example, as illustrated in FIG. 5, in some embodiments, tracks 146 can be located on vertical appendage 140 and/or horizontal appendage 142.

An exemplary track system can be configured to allow claws 118 to engage in one or more valleys 150 between adjacent teeth 148. In some embodiments, teeth 148 can have a generally rounded or oval surface preventing claw leverage onto the plunger. Each valley 150 between adjacent teeth 148 can be spaced a predetermined distance 152 from the next valley 150.

In other embodiments, teeth 148 can be configured to have a generally wave-like shape. When a claw is engaged in a valley 150 with a long front surface and a short back surface, claws 118 can provide force against the short wall of teeth 148. In some embodiments, an accessory 100 can include a plunger that has tracks that can be used with accessory 100. When a plunger is provided, the syringe plunger can be replaced with the provided plunger.

In other embodiments, a track or set of tracks can be provided to be attached to a plunger. In these embodiments, tracks can be glued to the plunger stem prior to use. In other embodiments, tracks can be snapped around a plunger stem.

Each valley 150 between adjacent ratcheting teeth 148 can be spaced 152 from the next valley. Each space 152 can be equivalent to a predetermined amount of substance ejected from the syringe. This is the case because movement of track 146 a particular distance moves plunger 126 which eventually moves plunger head 128 the same axial distance.

Accessory 100 can be formed of metal, a polymer, or a combination thereof. In some embodiments, accessory 100 can include materials such as, but not limited to, rigid thermoplastics, thermoplastic elastomers, silicones, glass, metals, composite materials, carbons fillers, or any combination thereof.

The accessories described herein can allow an operator to easily inject viscous substances or materials through any size needle known in the art by applying substantially perpendicular force to the handle. The accessories make the syringe easy to hold, manipulate and operate with one hand, and in some cases adjust easily with the operator's opposing hand. The accessories can allow the operator to precisely control the injection speed (or extrusion rate) being injected. The accessories can also allow an operator to still see the graduation or volume markings on the syringe body thereby allowing an operator to visualize initial volume, volume injected and remaining volume of substance in the syringe.

Further, the accessories described herein can have an ergonomic shape that allows the operator to hold and inject from the syringe easily. Unlike traditional syringes which do not conform to any ergonomic aspect of the hand, the present devices can have at least one ergonomic design shaped into the accessories such as finger indentation region 112. Additionally, the present accessories can accommodate operator hands of different sizes. Hand size accommodation can be accomplished by different device sizes, position-adjustable device handles or interchangeable device handles. For example, interchangeable handles can come in various pre-determined sizes or can be personalized for a particular user.

Figure 3:
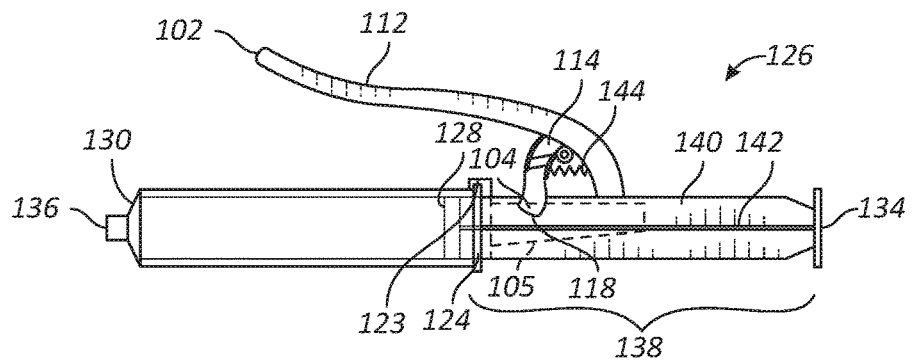
FIG. 3 illustrates a first step in using an extrusion accessory wherein the accessory is added to the syringe and prepared for use.

Methods of using the accessories described are also contemplated. For example, in some embodiments, an accessory is provided and attached to a syringe preferably at the syringe flange 124 as illustrated in FIG. 3. Spring 144 can be configured to rest handle 102 at a predetermined angle 132 relative to syringe 122 with claws 118 resting against plunger stem 138.

Figure 4:
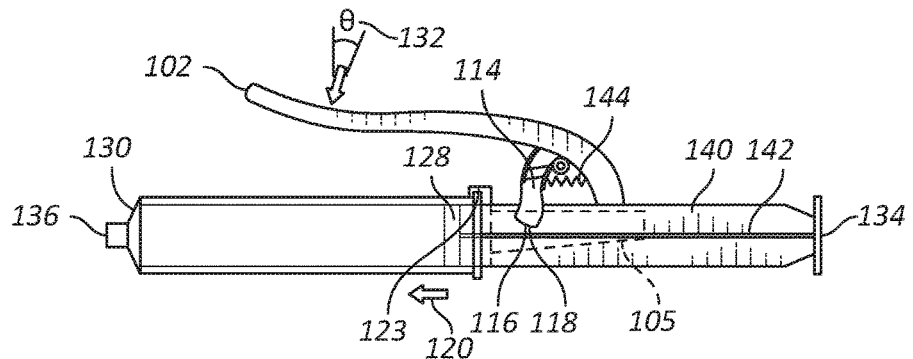
FIG. 4 illustrates a second step in using an extrusion accessory wherein a substantially perpendicular force is applied to the accessory's handle thereby applying an axial force to the syringe's plunger.

Then, as illustrated in FIG. 4, force is applied to handle 102 substantially perpendicular to syringe 122, thereby driving axial force to plunger 126 as translated by pawl 104.

When a particular spring force has been exhausted or a stop 154 on the underside of handle 102 has been reached, plunger 126 will not be moved axially any further as illustrated in FIG. 5. At this point, a full extension of accessory 100 has been achieved.

In other embodiments, full extension of accessory 100 can be achieved when pawl 104 abuts handle 102 at leading edge 162.

The force applied to move from predetermined angle 132 illustrated in FIG. 3 to the full extension of accessory 100 in FIG. 5 can translate into a predetermined dose of extruded content. For example, the force can translate into about 0.1 mL, about 0.5 mL, about 1 mL, about 2 mL, about 3 mL, about 4 mL, about 5 mL, about 10 mL, about 15 mL, about 20 mL, between about 0.1 mL and about 10 mL, between about 1 mL and about 10 mL, or between about 0.5 mL and about 5 mL. In other embodiments, a second stop 156 can be supplied such that pawl 104 can only travel between second stop 156 and stop 154. This distance of pawl 104 travel can be equivalent to an extruded amount from syringe 122.

For example, in some embodiments, predetermined distance 152 can define a dosage of substance because predetermined distance 152 can cause axial movement of plunger head 128 a second pre-determined distance 160. This second pre-determined distance 160 in turn represents a particular volume of substance extruded from syringe 122.

In other embodiments, the use of accessory 100 may not deliver a predetermined amount of substance or material but rather the amount delivered may still require use of visual marks on syringe 122.

In any circumstance, whether pre-determined or manual delivery amounts, once full extension of accessory 100 is achieved, claws 118 can be disengaged from plunger 126 by pulling handle 102 upward and away from syringe 122 as illustrated in FIG. 6. This disengagement can "re-set" the accessory to reengage the plunger 126 and deliver a subsequent dose of substance or material.

In some embodiments, when spring 144 is used, the upward force 158 needed to disengage claws 118 from plunger 126 can be reduced. Also, using spring 144 can pull pawl 104 toward handle 102 thereby "re-setting" accessory 100 for subsequent delivery.

Kits including an accessory as described herein are also contemplated. A kit can include an accessory that is configured to be attached to a syringe and instructions for use. In other embodiments, a kit can include an accessory, a syringe and instructions for use. In still other embodiments, a kit can include an accessory, a syringe filled with an injectable substance or a separate vial including the substance, and instructions for use. In other embodiments, a kit can include a syringe including an integrated accessory. In other embodiments, a kit can include a syringe including an integrated accessory and an injectable substance within the syringe or in a vial in the kit.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A syringe extrusion accessory couplable to a conventional syringe, the syringe comprising a cylindrical body, a flange portion extending radially outwardly from the cylindrical body at a distal end portion thereof, and a plunger reciprocally disposed within the cylindrical body, the accessory comprising:
   a handle operatively coupled to an attachment portion of the accessory, the attachment portion being configured to attach to the flange portion of the syringe; and
   at least one pawl having a first end and a second end, the at least one pawl (1) being hingedly and rotatably coupled relative to the handle at a first position at the first end and further attached to the handle at a second position between the first end and the second end, and (2) including a split for straddling a portion of the plunger and configured to directly engage with opposing sides of the plunger,
   wherein the syringe extrusion accessory is configured to transfer a substantially perpendicular force applied to the handle to an axial force to cause the at least one pawl to push the plunger of the syringe and extrude a product from the syringe.

2. The syringe extrusion accessory of claim 1, wherein the at least one pawl includes at least one claw.

3. The syringe extrusion accessory of claim 1, wherein the at least one pawl has a sinusoidal shape.

4. The syringe extrusion accessory of claim 1, wherein the handle is coupled to the attachment portion through a hinge.

5. The syringe extrusion accessory of claim 1 wherein the at least one pawl is spring-coupled to the handle through a compression spring.

6. The syringe extrusion accessory of claim 1, wherein the substantially perpendicular force is applied between about 1 degree and about 20 degrees perpendicular to the syringe.

7. The syringe extrusion accessory of claim 1, wherein the attachment portion is configured to attach to the flange portion of the syringe by a snap fit, a friction fit, a glue, an adhesive, or a combination thereof.

8. The syringe extrusion accessory of claim 1, wherein the handle includes a depression configured to apply force from at least one finger.

* * * * *